(12) United States Patent
Williamson

(10) Patent No.: US 9,724,496 B2
(45) Date of Patent: Aug. 8, 2017

(54) INTRAVASCULAR BALLOON AND DEFLATION WIRE

(71) Applicant: C. R. BARD, INC., Tempe, AZ (US)

(72) Inventor: Steve Williamson, Scottsdale, AZ (US)

(73) Assignee: C.R. Bard, Inc., Murray Hill, NJ (US)

( * ) Notice: Subject to any disclaimer, the term of this patent is extended or adjusted under 35 U.S.C. 154(b) by 205 days.

(21) Appl. No.: 14/497,207

(22) Filed: Sep. 25, 2014

(65) Prior Publication Data

US 2016/0089518 A1 Mar. 31, 2016

(51) Int. Cl.
*A61M 25/10* (2013.01)
*A61M 29/02* (2006.01)
*A61F 2/24* (2006.01)

(52) U.S. Cl.
CPC .......... *A61M 25/10184* (2013.11); *A61F 2/24* (2013.01); *A61M 25/104* (2013.01); *A61M 29/02* (2013.01); *A61M 2025/1093* (2013.01)

(58) Field of Classification Search
CPC . A61F 2/24; A61M 25/104; A61M 25/10184; A61M 29/02; A61N 25/104

USPC .......................................... 604/99.01, 164.05
See application file for complete search history.

(56) References Cited

U.S. PATENT DOCUMENTS

| | | | | |
|---|---|---|---|---|
| 3,402,718 A | * | 9/1968 | Doherty ................ | A61M 16/04 128/207.15 |
| 3,985,139 A | * | 10/1976 | Penar .................... | A61M 25/10 604/915 |
| 5,724,994 A | * | 3/1998 | Simon ................... | A61F 2/0009 128/885 |
| 6,355,013 B1 | * | 3/2002 | van Muiden ......... | A61M 25/10 604/164.05 |
| 2008/0249534 A1 | * | 10/2008 | Gruber .................. | A61B 1/303 606/119 |
| 2010/0318027 A1 | * | 12/2010 | Bierhoff ............... | A61B 17/221 604/96.01 |
| 2015/0051631 A1 | * | 2/2015 | Gould ................ | A61B 17/0218 606/192 |

* cited by examiner

*Primary Examiner* — Julie A Szpira
(74) *Attorney, Agent, or Firm* — C. R. Bard Intellectual Property Buchalter

(57) ABSTRACT

Angioplasty or valvuloplasty balloon catheters with a ripcord for cutting, ripping, or tearing a balloon can achieve faster deflation times. Methods using such catheters can improve patient outcomes in percutaneous transluminal valvuloplasty and angioplasty.

22 Claims, 8 Drawing Sheets

INTRAVASCULAR BALLOON AND DEFLATION WIRE

BACKGROUND

In various medical procedures, a clinician introduces a guiding catheter into a body lumen of a patient and advances the catheter through the lumen until the distal end of the catheter comes to rest near a desired location. For instance, in typical percutaneous transluminal coronary angioplasty (PTCA) procedures, a clinician percutaneously introduces a guiding catheter into a patient's cardiovascular system through the brachial or femoral artery and advances the catheter until the catheter's distal tip rests in the ostium of the desired artery. Similarly, in minimally invasive valvuloplasty, a balloon is inserted through the patient's vasculature until the balloon is positioned to treat (dilate) a heart valve.

When the valvuloplasty procedure goes as planned, it reestablishes acceptable operation of the valve or prepares the valve region for placement of a prosthetic valve. But complications can arise. For instance, the patient can become distressed needing rapid restoration of blood flow to downstream organs. Such situations call for rapid deflation of the balloon. Also, the balloon-catheter device can become stuck in the target lumen. What is needed is a device that can be rapidly deflated or cut to facilitate its removal from a target lumen or valve while retaining its retractability into a catheter sheath after deflation.

SUMMARY

The present disclosure provides percutaneous balloon angioplasty, venoplasty, or valvuloplasty balloons, balloon catheters, and balloon catheter handles that can accomplish rapid-deflation functionality.

A typical embodiment encompasses a catheter with a proximally located handle and a distal end with an attached balloon. The catheter has an inflation lumen in fluid communication with the inside of the balloon. A ripcord is attached through the ripcord's distal end. It attaches to the balloon's inner surface at one or more attachment points. The ripcord's proximal end sits near the catheter body's proximal end. In use, manipulation of the ripcord rapidly deflates the balloon.

In some embodiments, deflation occurs because the ripcord cuts, rips, or tears the balloon in a controlled manner when the ripcord is pulled proximally.

In some of these or other embodiments, the balloon wall comprises discrete portions that are weaker than surrounding portions and the ripping, tearing, or cutting occurs within the weaker, discrete, wall portions.

In some of these or other embodiments, the catheter has an anchor point located on the catheter body, inside and near the balloon's proximal end. In some embodiments, the balloon has an attachment point located on its inside surface. The attachment point may be distal to the anchor point. In some embodiments, the ripcord attaches to the attachment point and to the anchor point.

In some of these or other embodiments, the catheter body additionally comprises a ripcord lumen through which the ripcord passes. Sometimes, the ripcord lumen is disposed inside of the catheter body, and sometimes, the ripcord lumen is disposed outside of the catheter body.

Various embodiments exist in which the balloon is a compliant, non-compliant, or fiber-reinforced balloon.

In some embodiments, the balloon is adapted for use in a valvuloplasty procedure having the correct size, shape, and strength to dilate a heart valve.

The present disclosure provides methods of supplying an invention catheter and manipulating the ripcord to cause a controlled rip, tear, or cut through a portion of the balloon wall. In some of these embodiments, the method has steps of providing an invention catheter, introducing the catheter into a biological lumen, performing a procedure, and then rapidly deflating the balloon by causing a controlled rip, tear, or cut to form through a portion of the balloon wall.

DETAILED DESCRIPTION

The following describes non-limiting examples that further illustrate the invention. No section titles, including those appearing above, are limitations on the invention, but rather they provide structure to the illustrative descriptions that the specification provides. The features, aspects, and advantages of the invention will become more apparent from the following detailed description, appended claims, and accompanying drawings.

Unless defined otherwise, all technical and scientific terms used in this document have the same meanings that one skilled in the art to which the disclosed invention pertains would ascribe to them. The singular forms "a", "an", and "the" include plural referents unless the context clearly indicates otherwise. Thus, for example, reference to "a fluid" refers to one or more fluids, such as two or more fluids, three or more fluids, etc. Any mention of an element includes that element's equivalents as known to those skilled in the art.

The figures are not necessarily drawn to scale, and in some instances the drawings exaggerate or simplify the invention for illustrative purposes. One of ordinary skill in the art will appreciate the many possible applications and variations of the present invention based on the following examples of possible embodiments of the present invention.

The ripcord balloon of this invention facilitates the rapid removal of catheter-balloon combinations from a distressed patient, facilitates the removal of catheter-balloon combinations that have become stuck, out-performs competitive designs (thereby saving time during the procedure), and limits the time that a procedure restricts blood flow to vital organs.

Figure 1:
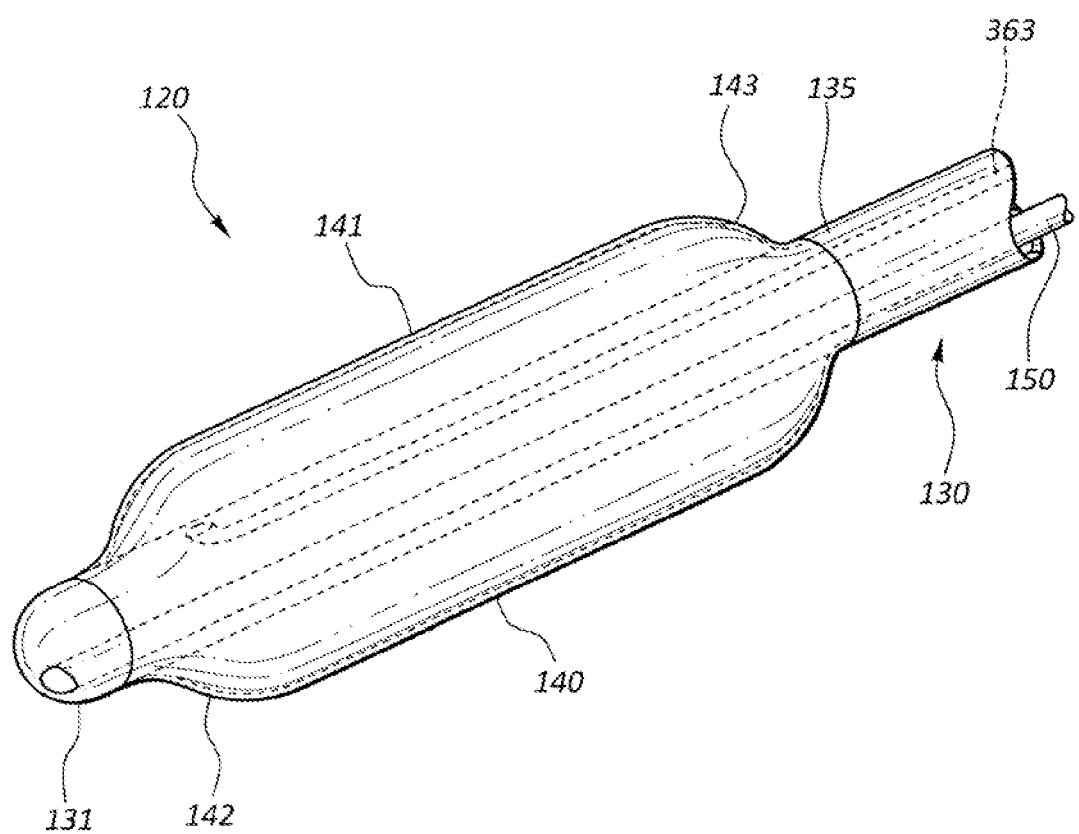
FIG. 1 is a perspective view of a prior art angioplasty balloon.

FIG. 1 shows a perspective view of a prior art medical balloon associated with a catheter 120 for use in percutaneous medical procedures. Catheter 120 comprises an elongate body 130 and an expandable balloon 140. Body 130 has a closed distal end 131 that is used as a probe for delivering catheter 120 to the target lumen. Body 130, of course, could have a channel or lumen 150 for receiving a guidewire. At least one lumen, inflation lumen 363, provides passage for a pressurized fluid into the interior of balloon 140. Balloon 140 comprises a thin membrane 141 that connects to the external wall 135 of body 130 at tapered distal region 142 and tapered proximal region 143, both of these regions composing part of balloon 140. Alternatively, thin membrane 141 is sometimes called balloon wall 900.

Figure 2:
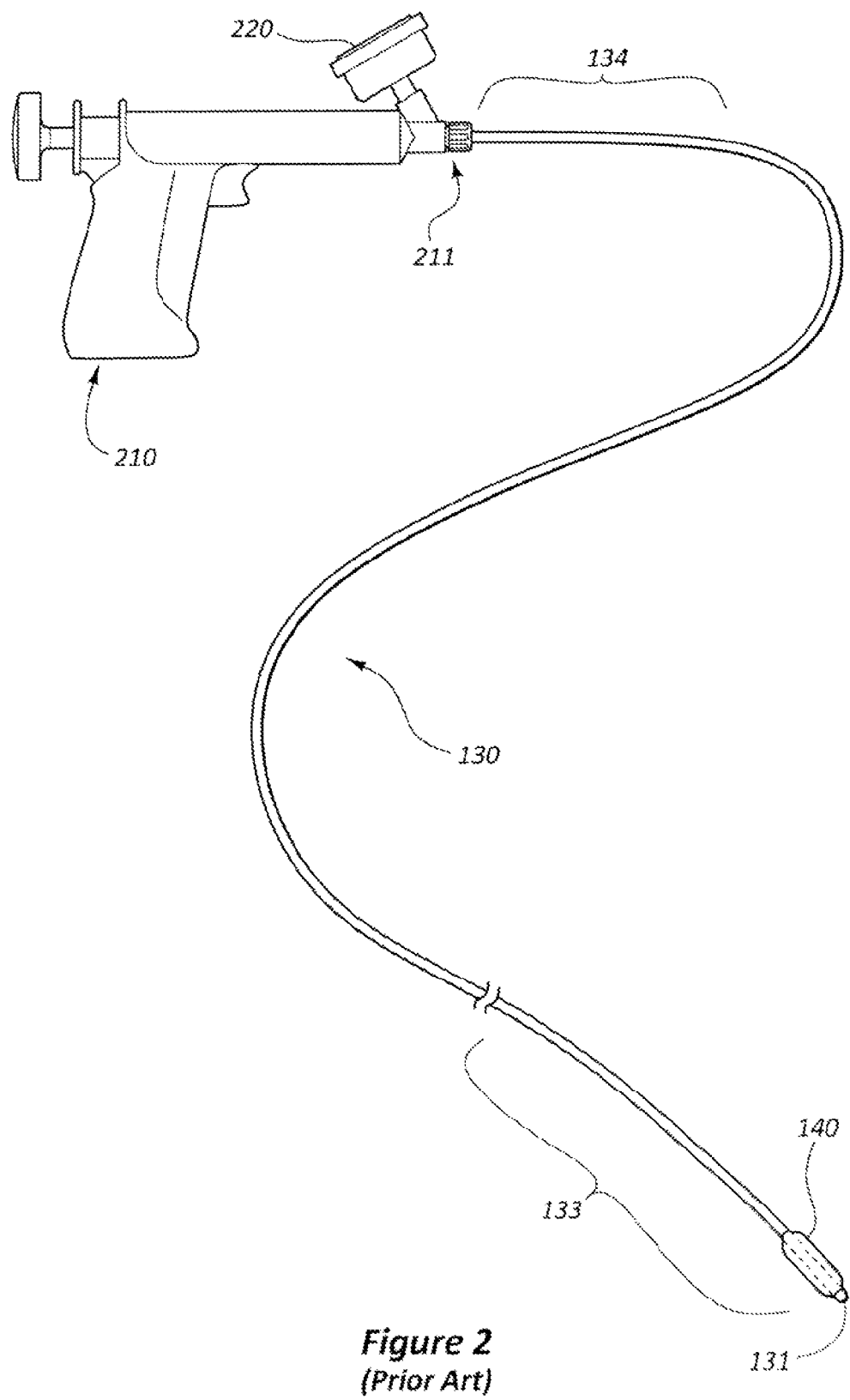
FIG. 2 is a schematic view of a prior art angioplasty balloon delivery system.

FIG. 2 shows a prior art medical balloon 140 mounted on a distal section 133 of body 130 with the proximal section 134 of body 130 terminating at the distal end 211 of a handle 210. Handle 210 comprises a port 220 that accesses the interior of body 130.

Figure 3A:
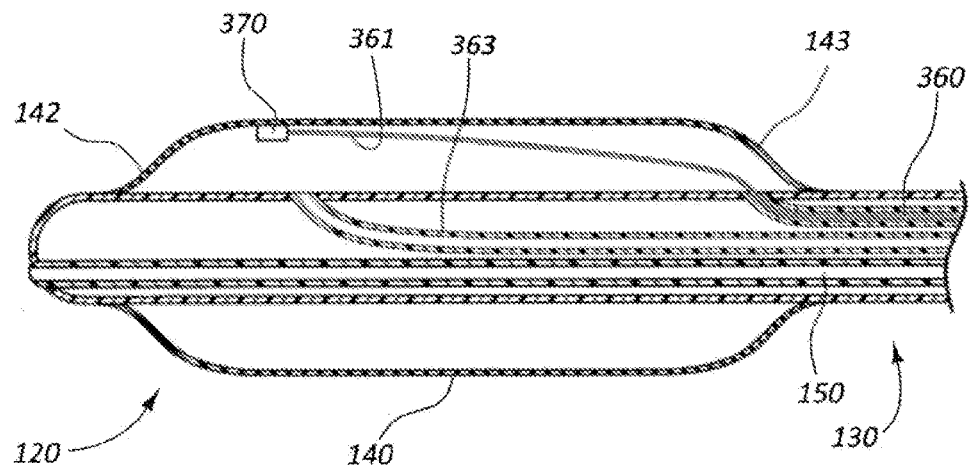
FIG. 3A is a schematic view and FIG. 3B is a perspective view of an embodiment of a balloon of the invention.
Figure 3B:
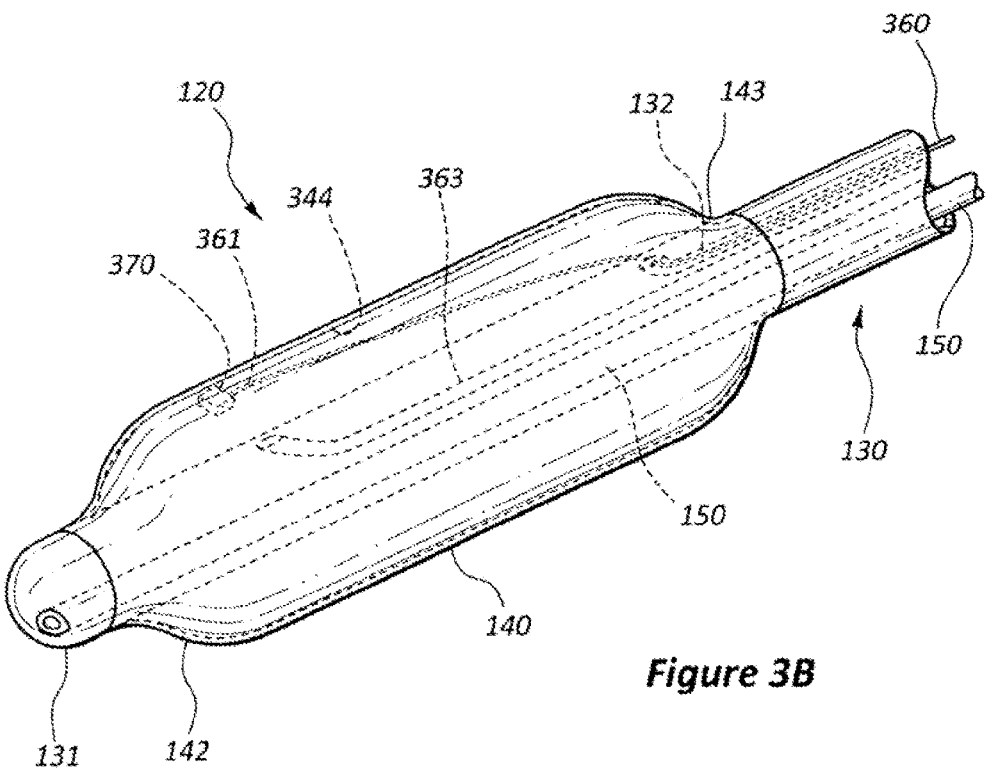

FIGS. 3A and 3B depict an embodiment of an invention device. Invention devices pertain to a catheter 120 comprising a body 130, a handle (not shown) connected to the proximal end (not shown) of body 130, optionally, a guidewire lumen 150 extending through at least part of body 130, a balloon 140 mounted near the distal end 131 of body 130, and an inflation lumen 363 extending from inside of balloon 140 to an exit (not shown) in or near the handle. Those of ordinary skill in the art know well the myriad guidewires suitable for use with those embodiments comprising guidewire lumen 150.

Figure 4:
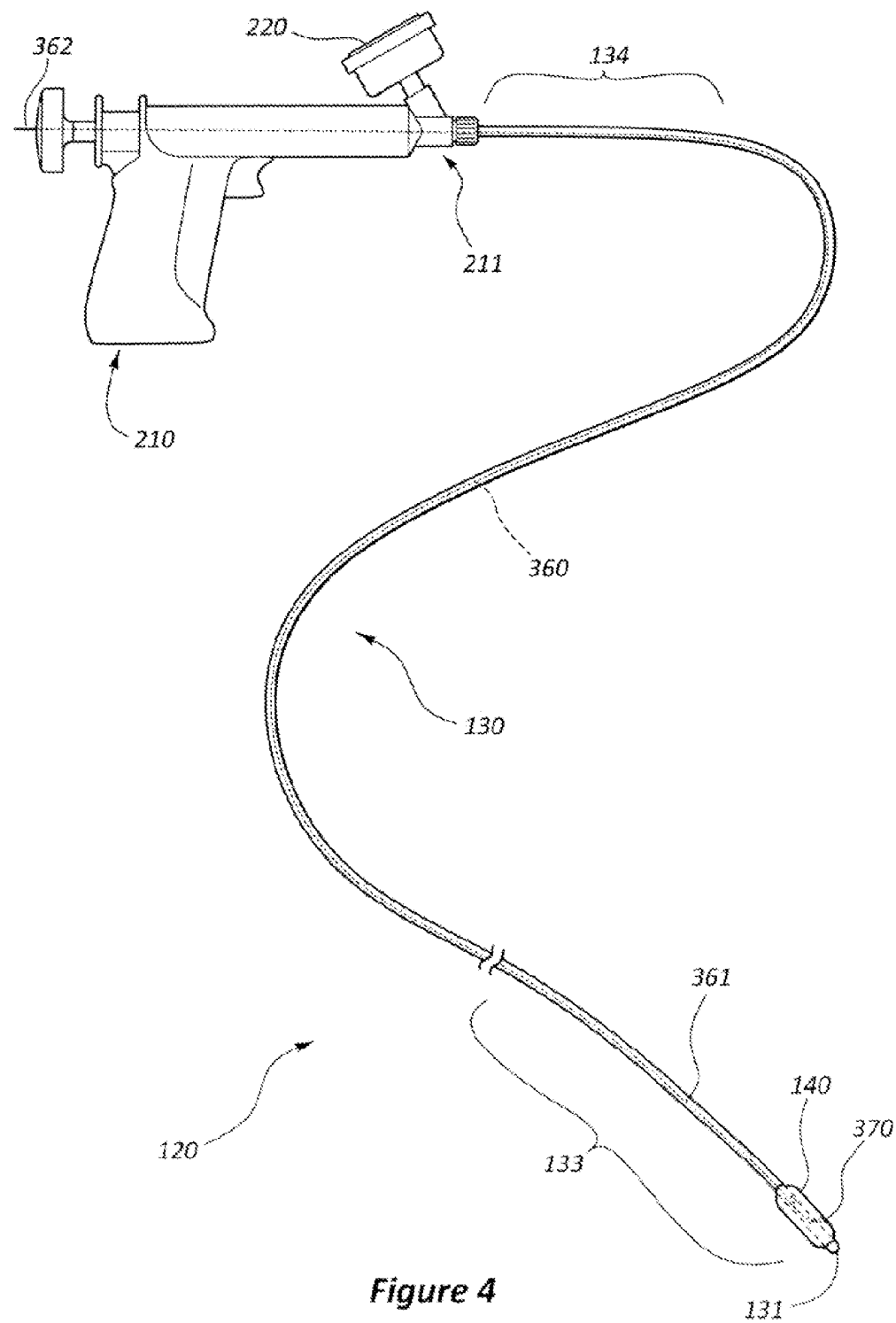
FIG. 4 is a schematic view of an embodiment of a balloon catheter delivery system of the invention.

Body 130 additionally comprises a ripcord 360, which can be a flexible, elongate member with a distal end 361 that attaches at an attachment region 370. Attachment region 370 attaches at an interior surface 344 of balloon 140. FIG. 4 shows an embodiment in which a proximal end 362 of ripcord 360 operably connects to handle 210 or passes through handle 210.

Ripcord 360 need not extend completely through body 130. In some embodiments, ripcord 360 passes through the wall of body 130 and exits the patient's body leaving ripcord proximal end 362 outside of the patient. This is sometimes called an early-exit embodiment. Sometimes ripcord 360 passes through the wall of body 130 proximal of balloon 140. And sometimes ripcord 360 passes through the wall of body 130 outside of the patient's body.

Figure 5A:
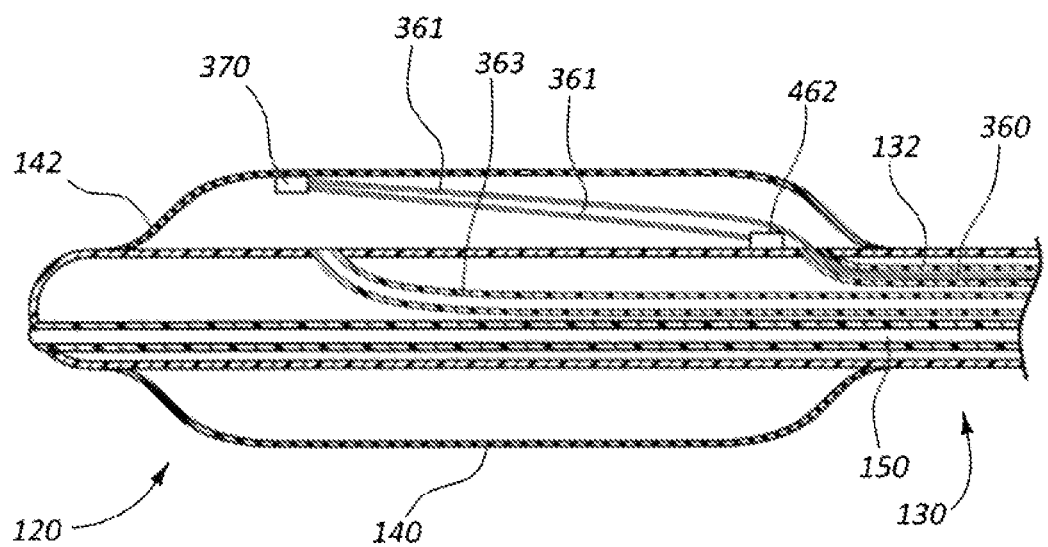
FIG. 5A is a schematic view and FIG. 5B is a perspective view of an embodiment of a balloon of the invention comprising an alternative ripcord configuration.
Figure 5B:
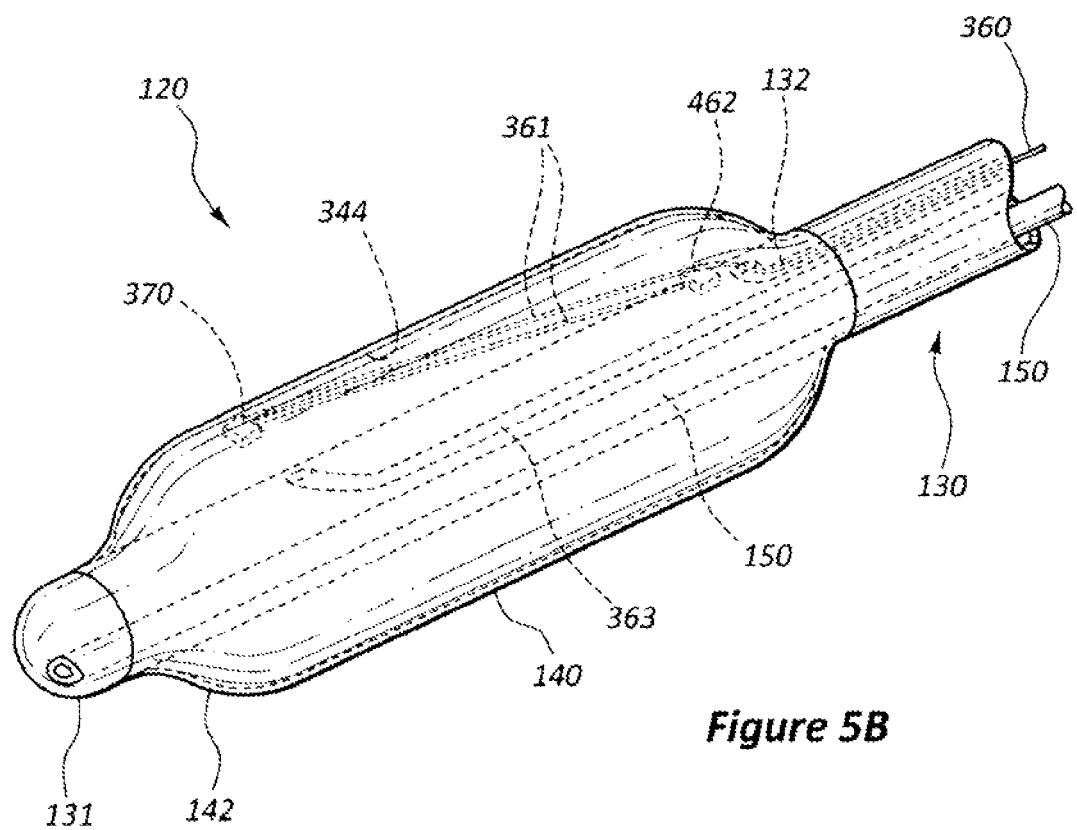

FIGS. 5A and 5B depict an alternate embodiment of an invention device showing an alternative configuration of ripcord 360. In this type of embodiment, ripcord 360 runs from the handle of catheter 120, distally through body 130, into the interior of balloon 140 or ripcord 360 uses an early-exit embodiment, as described above. Ripcord 360 attaches to interior surface 344 of balloon 140 at attachment region 370 after which distal end 361 of ripcord 360, while remaining inside of balloon 140, turns proximally and ends at anchor point 462. In some embodiments, ripcord 360 interacts with attachment region 370 in a slidable fashion.

In various embodiments, anchor point 462 sits proximal of attachment region 370. It can also sit on or at body 130 in some embodiments. Anchor point 462 can be securely fastened anywhere inside of balloon 140 such as proximal to attachment region 370. In some embodiments, distal end 361 of ripcord 360 extends directly between anchor point 462 and attachment region 370.

Figure 6:
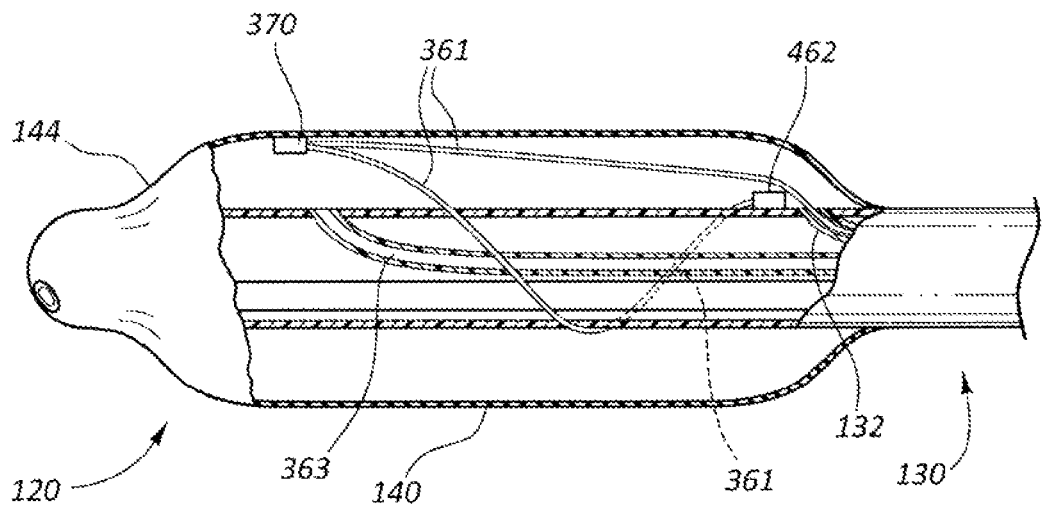
FIG. 6 is a schematic view of an embodiment of a balloon of the invention in which the ripcord wraps around the catheter's inner body.

In other embodiments, as depicted in FIG. 6, the distal end of ripcord 360 partially or completely wraps around body 130 and extends between anchor point 462 and attachment region 370.

Figure 7:
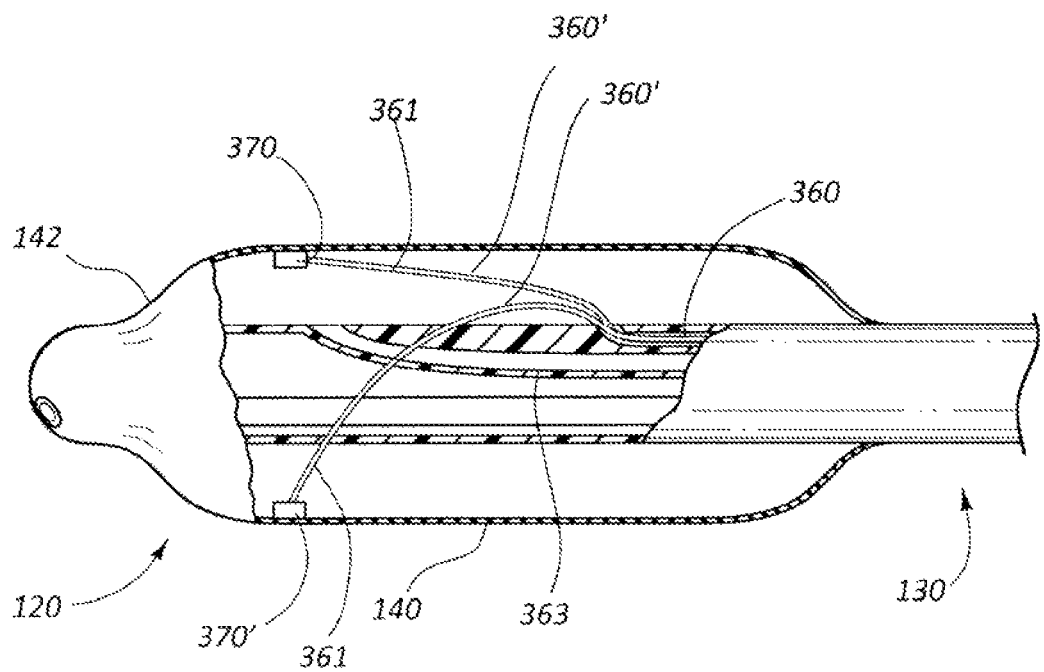
FIG. 7 is a schematic view of an embodiment of a balloon of the invention comprising two ripcords.

An alternative invention embodiment, shown in FIG. 7, uses a bifurcated ripcord 360' or two ripcords 360' situated at different attachment regions 370, 370'. The two ripcords join to a single, elongate member (ripcord 360) proximally of attachment regions 370, 370'. After two ripcords 360' join into ripcord 360, ripcord 360 extends proximally through body 130 exiting catheter 120 proximal of handle 210's proximal end. Or ripcord 360 can extend proximally as in an early-exit embodiment. Alternatively, the ripcord divides into two cords distal of the distal end of ripcord lumen 132. In various embodiments, ripcords 360' join distally or proximally to the proximal end of balloon 140. Of course, the two ripcord embodiments can be combined with embodiments using an anchor point and can be wrapped around body 130 as well, either using an early-exit embodiment or not.

Figure 8:
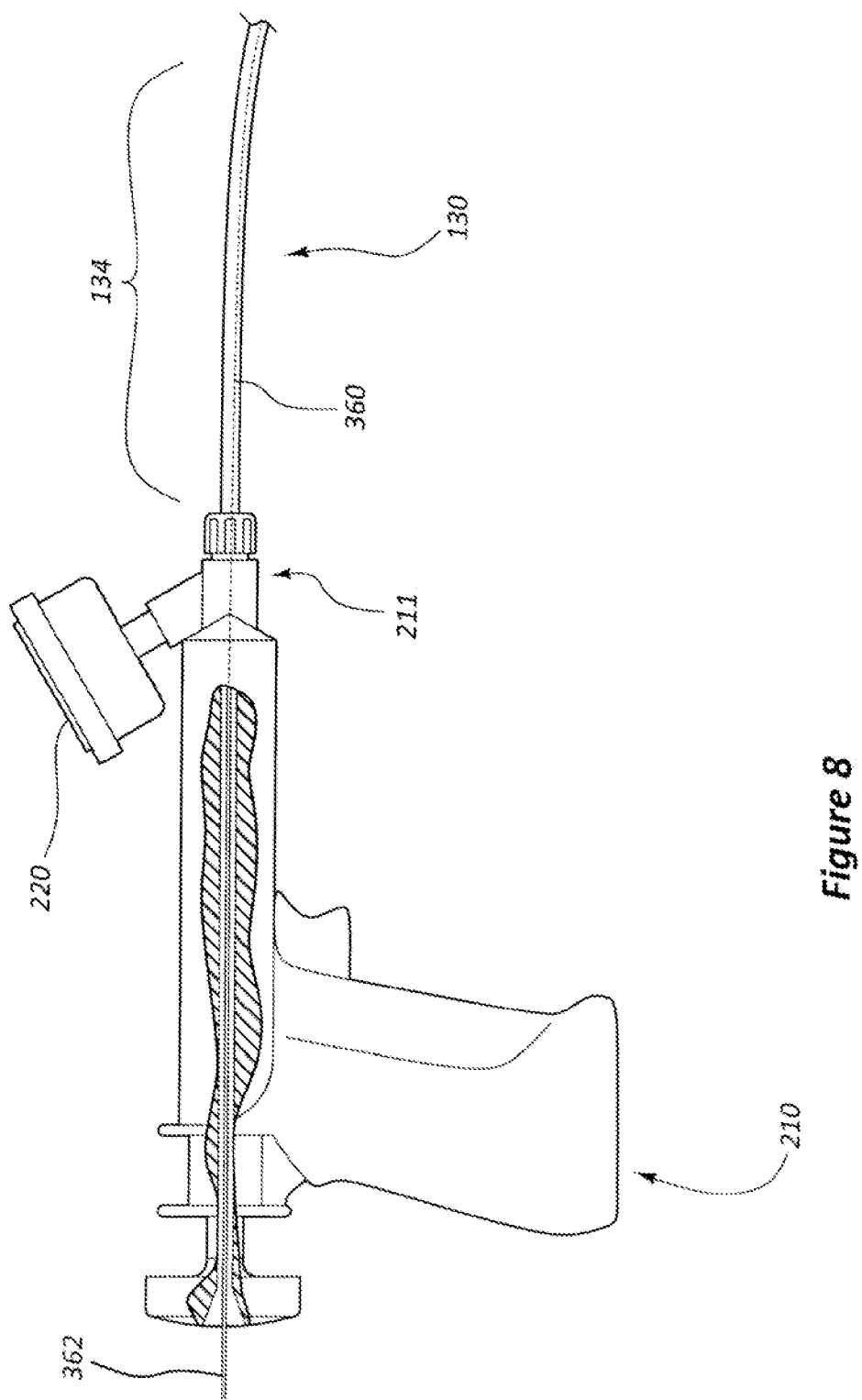
FIG. 8 is a schematic view of an embodiment of a balloon catheter handle of the invention.

FIG. 8 depicts handle 210. In this embodiment, proximal end 362 extends through handle 210. This is a way to allow ripcord 360 to be manipulated from outside of a patient's body.

In these or other embodiments, ripcord 360 runs through ripcord lumen 132. Ripcord 360 continues on to attachment region 370. Then ripcord 360 extends proximally to connect at anchor point 462. In some embodiments, inflation lumen 363 is also used as the ripcord lumen.

Figure 9:
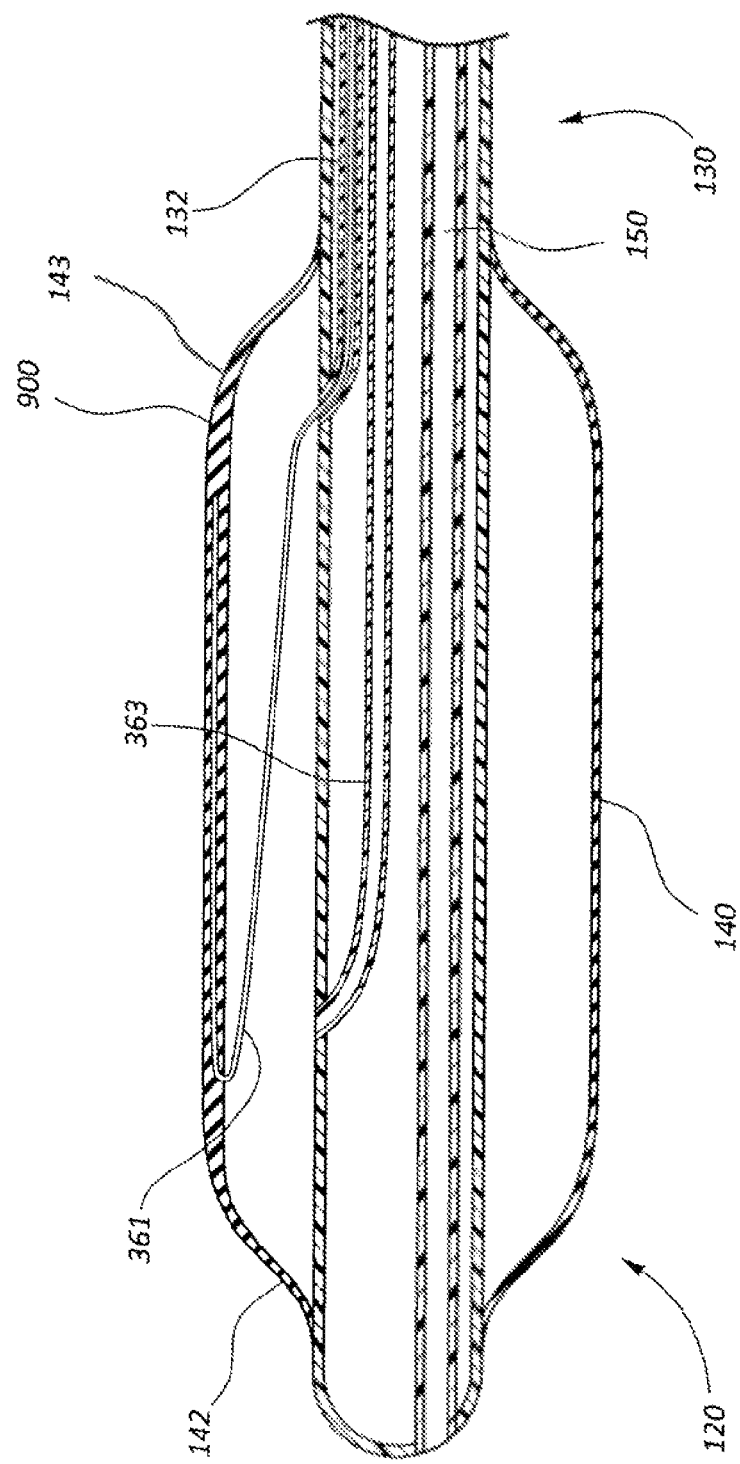
FIG. 9 is a schematic view of an embodiment of a balloon catheter with a ripcord embedded in the balloon wall.

FIG. 9 depicts an invention embodiment in which distal end 361 of ripcord 360 is embedded in balloon wall 900. This arrangement facilitates control over where the tear occurs and over the tear's length. Various embodiments exist in which distal end 361 of ripcord 360 is embedded in balloon wall 900 along at least 90-99, 80-99, 70-99, 10-90, 20-90, 30-90, or 40-90 percent of the length of balloon 140.

Of course, embodiments exist in which ripcord 360 has various cross-sectional geometries. For instance, the cross-section can be circular, oval, square, rectangular (yielding a ribbon-like ripcord), crescent-shaped, tubular, triangular, or the like. In some embodiments, the cross-section is chosen to provide strength, flexibility, connectability, ease of manufacturing, or any number of other characteristics recognized as important by those of ordinary skill in the art.

The function of ripcord 360 dictates which materials are suitable for its construction. In some embodiments, materials composing ripcord 360 have one or more of the following characteristics: high enough strength to transmit enough pulling force to the balloon to tear the balloon, high enough strength to attach to the balloon to transmit the pulling force to the balloon, high enough strength to attach to a hand piece, high enough flexibility to track through animal vasculature, low enough degree of stretching in the axial direction to transmit the pulling force to the balloon, etc.

A variety of materials will meet any of these characteristics. Also, one of ordinary skill in the art recognizes that materials that lack one or more of these characteristics can be treated, constructed, or otherwise modified to overcome that lack. In some embodiments, ripcord 360 comprises a material selected from metals, polysaccharides (such as cotton, flax, linen), polypeptides (such as silk), plastics, glass, ceramics, carbon fibers, or mixtures or combinations of these.

In these or other embodiments, ripcord 360 comprises any one or any chemical or physical combination of metals, alloys, polymers, oligomers, polysaccharides, and ceramics. In some embodiments, ripcord 360 comprises one or more of ABS/nylons, ABS/polyvinyl chlorides, acrylonitrile-butadiene-styrenes, acrylonitriles, alumina fibers, aminosilanes, aramids, carbon nanotubes, Celcon®, ceramic fibers, Dacron®, Delrin®, ethylene vinyl acetates, ethylene vinyl alcohols, fluorinated ethylene propylenes, fluoropolymers, glycidilsilanes, hydroxysilanes, ionomers, isocyanate silanes, Kevlar®, latexes, Mylars®, nanoclays, Nylon 11, Nylon 12, Nylon 4/6, Nylon 6, Nylon 6/10, Nylon 6/12, Nylon 6/6, Nylon 6/66, Nylon 6/9, nylons, Pebax® 7033, Pellethanes®, polyacetylenes, polyacrylamides, polyacrylates, polyacrylenesulfides, polyacrylsulfones, polyamides, polybutylene terephthalates, polycaprolactams, polycaprolactones, polycarbonates, poly-D,L-lactic acids, poly-D-lactic acids, polyester/polyadipates, polyester/polycaprolactones, polyesters, polyether block amides, polyether block esters, polyetheretherketones, polyetherketones, polyethersulfones, polyethylene naphthalates, polyethylene terephthalates, polyethylenes, polyimides, polyimines, polylactic acids, poly-L-lactic acids, polymethylpentenes, polyolefin acrylates, polyolefins, polyoxymethylenes, poly-phenylene ethers, polyphenylene sulfides, polyphosphazines, polypropylenes, polypyrroles, polysiloxanes, polytetrafluorethylenes, polyurethanes, polyvinyl chlorides, polyvinylidene difluorides, rubber, silicones, styrene acrylonitriles, styrenic polymers, or trifluoroethylenes. The polymers can be cross-linked or not, as necessary or desired.

Any balloon 140 that can benefit from rapid deflation is suitable for use with ripcord 360. Various ripcord embodiments are suited for high- or low-compliance balloons, reinforced balloons, fiber-reinforced balloons, dilation balloons, or other types of balloons. In some embodiments, the surface of balloon 140 is embossed with a feature to help control where on balloon 140 the tear starts. In these or other embodiments, the balloon surface is embossed with a feature that helps control the path of the tear. In some reinforced balloons, the materials of the balloon and reinforcement are selected to allow the balloon to tear when pulled by ripcord 360. For instance, fibers can be embedded in balloon wall 900. In some embodiments, balloon reinforcement is arranged such that parts of the balloon body can tear when pulled by ripcord 360 while other parts resist tearing. This difference in tear behavior can guide where the tear starts or guide the tear's path. In some of these embodiments, fibers are embedded in balloon wall 900 or are affixed to a surface of balloon 140 longitudinally oriented. When the ripcord 360 acts at a region on balloon 140 between adjacent fibers, the fibers direct the tear longitudinally and fence it in.

In some embodiments, ripcord 360 is used with a valvuloplasty balloon. Ripcord embodiments can be used on any delivery catheter system consistent with rapid deflation of the balloon.

In operation, a clinician inserts an invention device into a patient's vasculature (or other body lumen) percutaneously. After that, the clinician advances catheter 120 through the lumen until fluoroscopy, MRI, ultrasound, or some other visualization method indicates that balloon 140 is positioned as the clinician desires. In some embodiments, advancing catheter 120 uses a guidewire. The clinician next introduces inflation fluid (liquid or gas) through inflation lumen 363 causing balloon 140 to expand. After a time, the clinician deflates balloon 140. But sometimes deflation occurs too slowly.

When the clinician desires to rapidly deflate balloon 140, the clinician activates ripcord 360 by pulling it proximally. This causes ripcord 360 to cause a controlled cut, rip, or tear through a portion of the balloon 140 (balloon wall 900) causing it to rapidly deflate. This deflation occurs rapidly, but controllably, and therefore, rapidly restores blood flow (or other fluid flow) through the target lumen or valve. In some embodiments, activation of ripcord 360 causes a controlled helical cut, rip, or tear through about half of the length of balloon 140.

After deflation, the clinician must retrieve torn or popped balloon 140. Therefore, in some embodiments, torn balloon 140 must be retractable into catheter 120 or a sheath on catheter 120. Such retraction normalizes the shape of balloon 140 to help prevent problems such as injuring the patient's vasculature that could occur as a clinician retracts catheter 120. Those embodiments in which about half of the length of balloon 140 is cut retain about half of the length of balloon 140 intact. The intact portion aids in retracting the deflated balloon into catheter 120 or a sheath on catheter 120.

Returning to FIGS. 3A and 3B, balloon 140 can attach to catheter body 130 by any convenient bonding method known in the art. For example, at the proximal and distal ends of balloon 140, balloon 140 tapers to a cylindrical section approximating the size of body 130 and bonds to body 130 using a bonding agent. "Bonding agents" include suitable adhesives and glues. The adhesive used for fixing balloon 140 to catheter 120 must fix and bond balloon 140 to catheter 120 tightly enough to prevent balloon 140 and catheter 120 from separating. An appropriate adhesive can be selected from commercially available adhesives, particularly commercially available medicinal adhesives such as cyanoacrylate-type adhesives, among others. Alternatively, ultrasonic welding can be used. Any other bonding means as is known in the art for attaching balloon 140 to body 130 may be used in invention embodiments.

In the present invention, the material of balloon 140 is any material having an appropriate elasticity, appropriate inflatability in the target lumen by fluid fed through the catheter, appropriate disinfectibility by typical disinfection processes, or appropriate strength. In various embodiments of the present invention the balloon material may comprise natural rubbers, synthetic rubbers, silicone rubbers, or other elastomers that have previously been used as balloon materials in the prior art. One of ordinary skill in the art will recognize that materials discovered in the future will perform equally well with those disclosed above.

The needs of the target vessel dictate the shape and size of balloon 140. Ordinarily, balloons like balloon 140, having a cylindrical, cap-like shape as shown in the drawings, are employed. To enable balloon 140's insertion into or through small blood vessels, the diameter of balloon 140 in the non-inflated state should be as small as possible. Other balloons that the manufacturer has designed for use predominately in larger vessels do not need smaller, non-inflated diameters.

Any type of catheter 120 functions with the present invention, so far as it can be inserted through the body to the target lumen. Many suitable catheter materials are known to those of ordinary skill in the art. For example, polyethylene, polyamides, polyvinyl chloride, polyvinyl alcohol, acetalized polyvinyl alcohol can be used. Catheters 120 can be prepared from these polymeric materials or other well-known materials according to known processing techniques.

The device of the present invention is subjected to disinfection according to customary procedures before use.

The different variations described above combine to form many embodiments. A sampling of those embodiments is set out below. These are examples only and are not meant to limit claim scope.

Various embodiments have a catheter with a non-compliant balloon and an unbifurcated ripcord. The ripcord passes through an attachment point and ends at an anchor point and proximally travels through a ripcord lumen from the treatment location to outside of the patient's body. The ripcord is constructed of a polymer. In these embodiments, the balloon has discrete portions of the wall that are weaker than the surrounding portions.

Various embodiments have a catheter with a fiber-reinforced balloon, a guidewire lumen, and an unbifurcated ripcord. The ripcord passes through an attachment point and ends at an anchor point and proximally travels through a ripcord lumen from the treatment location to outside of the patient's body. The ripcord is constructed of a polymer. In these embodiments, the balloon has discrete portions of the wall that are weaker than the surrounding portions.

Various embodiments have a catheter with a non-compliant balloon, a guidewire lumen, and an unbifurcated ripcord. The ripcord attaches to an attachment point and travels through a ripcord lumen from the treatment location to outside of the patient's body. The ripcord is constructed of a polymer. In these embodiments, the balloon has discrete portions of the wall that are weaker than the surrounding portions.

Various embodiments have a catheter with a non-compliant balloon and a bifurcated ripcord. The ripcord attaches to an attachment point and travels through a ripcord lumen from the treatment location to outside of the patient's body. The ripcord is constructed of polysaccharides. In these embodiments, the balloon has discrete portions of the wall that are weaker than the surrounding portions.

Various embodiments have a catheter with a non-compliant balloon, a guidewire lumen, and a bifurcated ripcord. The ripcord attaches to an attachment point and travels through a ripcord lumen from the treatment location to outside of the patient's body. The ripcord is constructed of a metal or alloy. In these embodiments, the balloon has discrete portions of the wall that are weaker than the surrounding portions.

Various embodiments have a catheter with a fiber-reinforced balloon, a guidewire lumen, and an unbifurcated ripcord. The ripcord attaches to an attachment point and travels through a ripcord lumen from the treatment location to outside of the patient's body. The ripcord is constructed of polysaccharides. In these embodiments, the balloon has discrete portions of the wall that are weaker than the surrounding portions.

Various embodiments have a catheter with a non-compliant balloon and an unbifurcated ripcord. The ripcord attaches to an attachment point and travels through a ripcord lumen from the treatment location to outside of the patient's body. The ripcord is constructed of a polymer.

Various embodiments have a catheter with a non-compliant balloon, a guidewire lumen, and an unbifurcated ripcord. The ripcord attaches to an attachment point and travels through a ripcord lumen from the treatment location to outside of the patient's body. The ripcord is constructed of a polymer.

Various embodiments have a catheter with a non-compliant balloon, a guidewire lumen, and an unbifurcated ripcord. The ripcord passes through an attachment point and ends at an anchor point and proximally travels through a ripcord lumen from the treatment location to outside of the patient's body. The ripcord is constructed of a polymer.

Various embodiments have a catheter with a non-compliant balloon and an unbifurcated ripcord. The ripcord attaches to an attachment point and travels through a ripcord lumen from the treatment location to outside of the patient's body. The ripcord is constructed of polysaccharides.

Various embodiments have a catheter with a non-compliant balloon, a guidewire lumen, and a bifurcated ripcord. The ripcord attaches to an attachment point and travels through a ripcord lumen from the treatment location to outside of the patient's body. The ripcord is constructed of a metal or alloy.

Various embodiments have a catheter with a non-compliant balloon and a bifurcated ripcord. The ripcord passes through an attachment point and ends at an anchor point and proximally travels through a ripcord lumen from the treatment location to outside of the patient's body. The ripcord is constructed of polysaccharides.

Various embodiments have a catheter with a non-compliant balloon, a guidewire lumen, and a bifurcated ripcord. The ripcord passes through an attachment point and ends at an anchor point and proximally travels through a ripcord lumen from the treatment location to outside of the patient's body. The ripcord is constructed of a polymer.

Various embodiments have a catheter with a non-compliant balloon, a guidewire lumen, and a ripcord that wraps around the catheter body. The ripcord passes through an attachment point and ends at an anchor point and proximally travels through a ripcord lumen from the treatment location to outside of the patient's body. The ripcord is constructed of a polymer.

Various embodiments have a catheter with a non-compliant balloon and a ripcord that wraps around the catheter body. The ripcord attaches to an attachment point and travels through a ripcord lumen from the treatment location to outside of the patient's body. The ripcord is constructed of polysaccharides.

Various embodiments have a catheter with a non-compliant balloon, a guidewire lumen, and a ripcord that wraps around the catheter body. The ripcord attaches to an attachment point and travels through a ripcord lumen from the treatment location to outside of the patient's body. The ripcord is constructed of a polymer.

Various embodiments have a catheter with a non-compliant balloon, a guidewire lumen, and an unbifurcated ripcord. The ripcord attaches to an attachment point and travels through a ripcord lumen from the treatment location to outside of the patient's body. The ripcord is constructed of a metal or alloy.

Various embodiments have a catheter with a fiber-reinforced balloon and an unbifurcated ripcord. The ripcord passes through an attachment point and ends at an anchor point and proximally travels through a ripcord lumen from the treatment location to outside of the patient's body. The ripcord is constructed of polysaccharides.

Various embodiments have a catheter with a fiber-reinforced balloon, a guidewire lumen, and an unbifurcated ripcord. The ripcord passes through an attachment point and ends at an anchor point and proximally travels through a ripcord lumen from the treatment location to outside of the patient's body. The ripcord is constructed of a metal or alloy.

Various embodiments have a catheter with a fiber-reinforced balloon, a guidewire lumen, and a bifurcated ripcord. The ripcord attaches to an attachment point and travels through a ripcord lumen from the treatment location to outside of the patient's body. The ripcord is constructed of a polymer.

Various embodiments have a catheter with a fiber-reinforced balloon and a bifurcated ripcord. The ripcord passes through an attachment point and ends at an anchor point and proximally travels through a ripcord lumen from the treatment location to outside of the patients body. The ripcord is constructed of polysaccharides.

Various embodiments have a catheter with a fiber-reinforced balloon and an unbifurcated ripcord. The ripcord passes through an attachment point and ends at an anchor point and proximally travels through a ripcord lumen from the treatment location to outside of the patient's body. The ripcord is constructed of a polymer.

Various embodiments have a catheter with a fiber-reinforced balloon, a guidewire lumen, and a bifurcated ripcord. The distal end of the ripcord is embedded in the balloon wall along 10-90 percent of the length of the balloon and proximally travels through a ripcord lumen from the treatment location to outside of the patient's body. The ripcord is constructed of a metal or alloy.

Various embodiments have a catheter with a fiber-reinforced balloon, a guidewire lumen, and an unbifurcated ripcord. The ripcord attaches to an attachment point and travels through a ripcord lumen from the treatment location to outside of the patient's body. The ripcord is constructed of a polymer.

Various embodiments have a catheter with a non-compliant balloon and an unbifurcated ripcord. The distal end of the ripcord is embedded in the balloon wall along 10-90 percent of the length of the balloon and proximally travels through a ripcord lumen from the treatment location to outside of the patient's body. The ripcord is constructed of a polymer.

Various embodiments have a catheter with a non-compliant balloon, a guidewire lumen, and an unbifurcated ripcord. The distal end of the ripcord is embedded in the balloon wall along 20-80 percent of the length of the balloon and proximally travels through a ripcord lumen from the treatment location to outside of the patient's body. The ripcord is constructed of polysaccharides.

Various embodiments have a catheter with a non-compliant balloon and an unbifurcated ripcord. The distal end of the ripcord is embedded in the balloon wall along 20-80 percent of the length of the balloon and proximally travels through a ripcord lumen from the treatment location to outside of the patient's body. The ripcord is constructed of a polymer.

Various embodiments have a catheter with a non-compliant balloon, a guidewire lumen, and a ripcord that wraps around the catheter body. The distal end of the ripcord is embedded in the balloon wall along 20-80 percent of the length of the balloon and proximally travels through a ripcord lumen from the treatment location to outside of the patient's body. The ripcord is constructed of a polymer.

Various embodiments have a catheter with a non-compliant balloon and an unbifurcated ripcord. The distal end of the ripcord is embedded in the balloon wall along 40-60 percent of the length of the balloon and proximally travels through a ripcord lumen from the treatment location to outside of the patient's body. The ripcord is constructed of a metal or alloy.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true, intended, explained, disclosed, and understood scope and spirit of this invention's multitudinous embodiments and alternative descriptions.

Additionally, various embodiments have been described above. For convenience's sake, combinations of aspects composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists that specifically excludes that aspect. All patents, test procedures, and other documents cited in this specification are fully incorporated by reference to the extent that this material is consistent with this specification and for all jurisdictions in which such incorporation is permitted.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically exclude the value or the conditions for the aspect.

The invention claimed is:

1. A catheter comprising:
   a body;
   a balloon having a length, a wall, a distal end, and a proximal end mounted near the distal end of the body;
   an inflation lumen extending from inside of the balloon to an exit in or near the proximal end of the body wherein the inflation lumen is in fluid communication with the inside of the balloon;
   and
   a ripcord attached at an attachment point to an interior surface of the balloon and having a proximal end that sits near the proximal end of the body such that proximal translation of the ripcord deflates the balloon by ripping, cutting, or tearing the balloon.

2. The catheter of claim 1 wherein the distal end of the ripcord is embedded in the balloon wall along 90-99, 80-99, 70-99, 10-90, 20-90, 30-90, or 40-90 percent of the length of the balloon.

3. The catheter of claim 2 wherein the balloon is substantially non-compliant.

4. The catheter of claim 3 wherein the balloon has a wall comprising reinforcing fibers.

5. The catheter of claim 3 wherein the balloon is adapted for use in a valvuloplasty procedure.

6. The catheter of claim 1 wherein ripping, cutting, or tearing the balloon occurs helically around the balloon surface through about half of the balloon length.

7. The catheter of claim 1 wherein discrete portions of the wall of the balloon are weaker than the surrounding portions and ripping, cutting, or tearing substantially occurs in the weaker discrete wall portions.

8. The catheter of claim 7 further comprising an anchor point located on the catheter body, inside and near the proximal end of the balloon, wherein
   the attachment point is distal to the anchor point
   and
   the ripcord has a distal end, a portion of which connects to the anchor point and a portion of which connects to the attachment point.

9. The catheter of claim 8 further comprising a ripcord lumen having a distal end through which the ripcord passes.

10. The catheter of claim 9 wherein the ripcord lumen is disposed outside of the catheter body.

11. The catheter of claim 9 wherein the ripcord lumen is disposed inside of the catheter body.

12. The catheter of claim 11 wherein the ripcord divides into two cords distal of the distal end of the ripcord lumen.

13. The catheter of claim 12 further comprising another attachment point.

14. The catheter of claim 8 wherein the balloon is substantially non-compliant.

15. The catheter of claim 14 wherein the balloon has a wall comprising reinforcing fibers.

16. The catheter of claim 8 wherein the balloon is adapted for use in a valvuloplasty procedure.

17. A catheter comprising:
an elongate body having proximal and distal ends;
a guidewire lumen extending through at least part of the body;
a substantially non-compliant balloon mounted near the distal end of the catheter;
an anchor point located on the catheter body, inside and near the proximal end of the balloon;
an attachment region attached to a surface of the balloon, distal to the anchor point;
an inflation lumen extending from inside of the balloon to an exit in or near a handle wherein the inflation lumen is in fluid communication with the inside of the balloon;
a ripcord attached to the attachment region, having a proximal end extending to an exit in or near the handle having a distal end connected to the anchor point and to the attachment region;
and
a ripcord lumen through which the ripcord passes,
wherein
proximal translation of the ripcord deflates the balloon by cutting, ripping, or tearing the balloon,
and
discrete portions of the wall of the balloon are weaker than the surrounding portions and cutting, ripping or tearing substantially occurs at the weaker discrete wall portions.

18. A method comprising:
supplying the catheter of claim 1;
manipulating the ripcord to cause a controlled cut, rip, or tear through a portion of the balloon wall;
and
retracting the cut, ripped, or torn balloon.

19. A method comprising:
providing a balloon catheter comprising
a body;
a handle connected to the proximal end of the body;
a balloon mounted near the distal end of the catheter;
an inflation lumen extending from inside of the balloon to an exit in or near the handle wherein the inflation lumen is in fluid communication with the inside of the balloon;
and
a ripcord attached at an attachment point to a surface of the balloon and having a proximal end which operably connects to the handle or near to the proximal end of the body such that proximal translation of the ripcord deflates the balloon,
and
introducing a balloon catheter into a biological lumen;
performing a procedure;
followed by
rapidly deflating the balloon by creating a controlled cut, rip, or tear through a portion of a wall of the balloon;
and
retracting the cut, ripped, or torn balloon.

20. The method of claim 19 wherein the controlled cut is a helical cut through about half of the balloon length.

21. A method of deflating a dilation balloon wherein the dilation balloon has a wall and composes part of a catheter, wherein the catheter additionally comprises a ripcord, and wherein the ripcord attaches to the balloon wall, the method comprising manipulating the ripcord to cause a controlled cut through a portion of the balloon wall.

22. The method of claim 21 wherein the controlled cut is a helical cut through about half of the balloon length.

* * * * *